United States Patent
Myers et al.

(10) Patent No.: US 6,471,167 B1
(45) Date of Patent: Oct. 29, 2002

(54) SURGICAL TRAY SUPPORT SYSTEM

(75) Inventors: Reese K. Myers, Warsaw, IN (US); Eric F. Dahlinger, Hawthorn Woods, IL (US); Timothy E. Wood, Weare, NH (US)

(73) Assignee: Poly Vac, Inc., Manchester, NH (US)

( * ) Notice: Subject to any disclaimer, the term of this patent is extended or adjusted under 35 U.S.C. 154(b) by 0 days.

(21) Appl. No.: 09/540,652

(22) Filed: Mar. 31, 2000

(51) Int. Cl.$^7$ .............................................. F16M 11/02
(52) U.S. Cl. .................. 248/177.1; 248/447.2; 248/125.9
(58) Field of Search ................ 248/447.2, 125.1, 248/125.8, 125.9, 157, 177.1

(56) References Cited

U.S. PATENT DOCUMENTS

| | | | | |
|---|---|---|---|---|
| 462,319 A | * | 11/1891 | Loehner et al. ......... | 248/231.41 |
| 2,377,949 A | | 6/1945 | McMenamy ................ | 248/122 |
| 2,585,647 A | | 5/1952 | DuMais et al. ............... | 160/24 |
| 2,678,792 A | * | 5/1954 | Gallion et al. ......... | 248/226.11 |
| 2,703,265 A | | 3/1955 | Wolfe ........................... | 311/27 |
| 2,904,798 A | | 9/1959 | Heflin ........................... | 5/317 |
| 3,054,122 A | * | 9/1962 | Sarkus ........................ | 108/49 |
| 3,086,226 A | | 4/1963 | Kyser et al. .................... | 5/332 |
| 3,272,464 A | | 9/1966 | Jacobson ..................... | 248/125 |
| 3,738,405 A | * | 6/1973 | Ericson ........................ | 108/90 |
| 3,859,993 A | * | 1/1975 | Bitner .......................... | 128/847 |
| 4,113,218 A | * | 9/1978 | Linder ...................... | 248/291.1 |
| 4,381,572 A | * | 5/1983 | Thumberger ................... | 5/651 |
| 4,466,596 A | * | 8/1984 | Cohen ........................ | 248/635 |
| 4,591,124 A | * | 5/1986 | Hellenbrand et al. .... | 248/447.1 |
| 4,725,027 A | | 2/1988 | Bekanich .................... | 248/125 |
| 5,019,124 A | * | 5/1991 | Flugger ....................... | 248/201 |
| 5,022,617 A | | 6/1991 | Henderson ................... | 248/125 |
| 5,152,486 A | * | 10/1992 | Kabanek et al. ............ | 206/564 |
| 5,170,804 A | * | 12/1992 | Glassman ................... | 128/849 |
| 5,362,021 A | * | 11/1994 | Phillips ................... | 248/276.1 |
| 5,538,215 A | | 7/1996 | Hosey ..................... | 248/286.1 |
| 5,628,078 A | | 5/1997 | Pennington et al. .......... | 5/618 |
| 5,681,018 A | | 10/1997 | Hoftman .................. | 248/125.8 |
| 6,213,435 B1 | * | 4/2001 | Minet ...................... | 248/125.8 |

FOREIGN PATENT DOCUMENTS

JP          11332922 A  * 12/1999

OTHER PUBLICATIONS

The Infant Cast Table, Midmark Corporation 1991, 1 pg.
Chick 703 Orthopaidic & Surgical Operating Table, Midmark Corporation 1995, 4 pgs.
Chick CLT, Chick–Langreri Orthopaidic & Surgical Operating Table, Midmark Corporation 1995, 4 pgs.
Chick, Midmark Imagable Orthopaedic Table, Midmark Corporation 1997, 4 pgs.
The Midmark 7100 General Surgery Table, Midmark 1994, 9 pgs.

* cited by examiner

Primary Examiner—Leslie A. Braun
Assistant Examiner—Naschica S. Morrison
(74) Attorney, Agent, or Firm—Taylor & Aust, P.C.

(57) ABSTRACT

A surgical instrument tray support assembly for attachment to a surgical table having a table frame and at least one side rail secured to the table frame. The surgical instrument tray support system includes a bracket for attachment to the side rail for supporting a post in a generally upright position. A top tube is slidably mounted over the post. Completing the assembly is a frame for supporting a surgical tray, and a bracket for attaching said frame to the top tube.

4 Claims, 5 Drawing Sheets

US 6,471,167 B1

SURGICAL TRAY SUPPORT SYSTEM

BACKGROUND OF THE INVENTION

1. Field of the Invention

The present invention relates to a surgical tray support system, and more particularly to a surgical tray support system for attachment to a surgical table.

2. Discussion of the Prior Art

It is normal procedure to provide appropriate types (styles) and quantities of surgical instruments and materials for a specific surgical procedure as a sterilized unitary package. Prior to or during an operation, the instruments and materials are removed from the package and positioned on a so-called Mayo stand or table or other surface so that they are accessible to the surgical scrub nurse or assistant who eventually passes the instruments or supplies to the surgeon. Frequently, due to patient positioning, operative site location, or other obstacles, the surgical team and Mayo stand are located in such a position as to make the transfer of instruments or supplies to the surgeon awkward, increasing the probability that an instrument or accessory (i.e. sponge, suture, implant, etc.) might be dropped, delayed or otherwise mishandled. This can be especially hazardous to the surgical team in the transfer of instruments or supplies with sharp ends or cutting edges.

A typical instrument package may include a basket or tray made of various materials including plastic or metal, in which the instruments are placed for sterilization and organization. Fixating means such as a finger mat, posts or fixtures may be provided to fix the positions of the instruments in the basket or tray so that the instruments do not become co-mingled or damaged when the basket or tray is moved about.

Natural efficiencies are created when the instruments are placed within easy and comfortable view of the surgeon or surgical assistant, so that the surgical team does not have to pass instruments back and forth, or wait for a properly identified instrument to be found and be provided. Also, the likelihood of accidental drops may be reduced if the instrument package or storage tray system is within easy reach of the surgeon or surgical team and the operative site.

SUMMARY OF THE INVENTION

The present invention provides a system for supporting surgical instrument trays within easy reach and view of the surgical team by supporting the tray affixed to a side rail of the surgical table. More particularly, in accordance with the present invention, there is provided a surgical tray support comprising a frame affixed to a support rod which in turn is affixed to the surgical table side rail. The frame is adjustable and can be moved on several planes. Most commonly, the frame is adjustable for horizontal swiveling and for tilting at an angle such as to make the instruments more visual and physically accessible, while not compromising stability. In a preferred embodiment, the support includes an upright or standard which is affixed through an adjustable coupling to the surgical table side rail. A top tube is slidably, removably mounted over the upright or standard, and a frame sized and shaped to accept the surgical tray is affixed to the top tube. Alternatively, the surgical tray support may be mounted to a free standing floor support or a Mayo stand or the like. The frame and the top tube are removable so that they may be subjected to sterilization along with the instrument and instrument tray.

In a preferred embodiment of the invention, the frame support is affixed to the removable top post by means of an articulated socket or the like which permits the tray to be tilted. Alternatively, the tray itself may be designed and manufactured with an angle to enhance visibility and accessibility when placed within the frame support.

BRIEF DESCRIPTION OF THE DRAWINGS

Further features and advantages of the invention will be apparent from the following detailed description, taken in conjunction with the accompanying drawings, wherein.

DETAILED DESCRIPTION OF THE INVENTION

Figure 1:
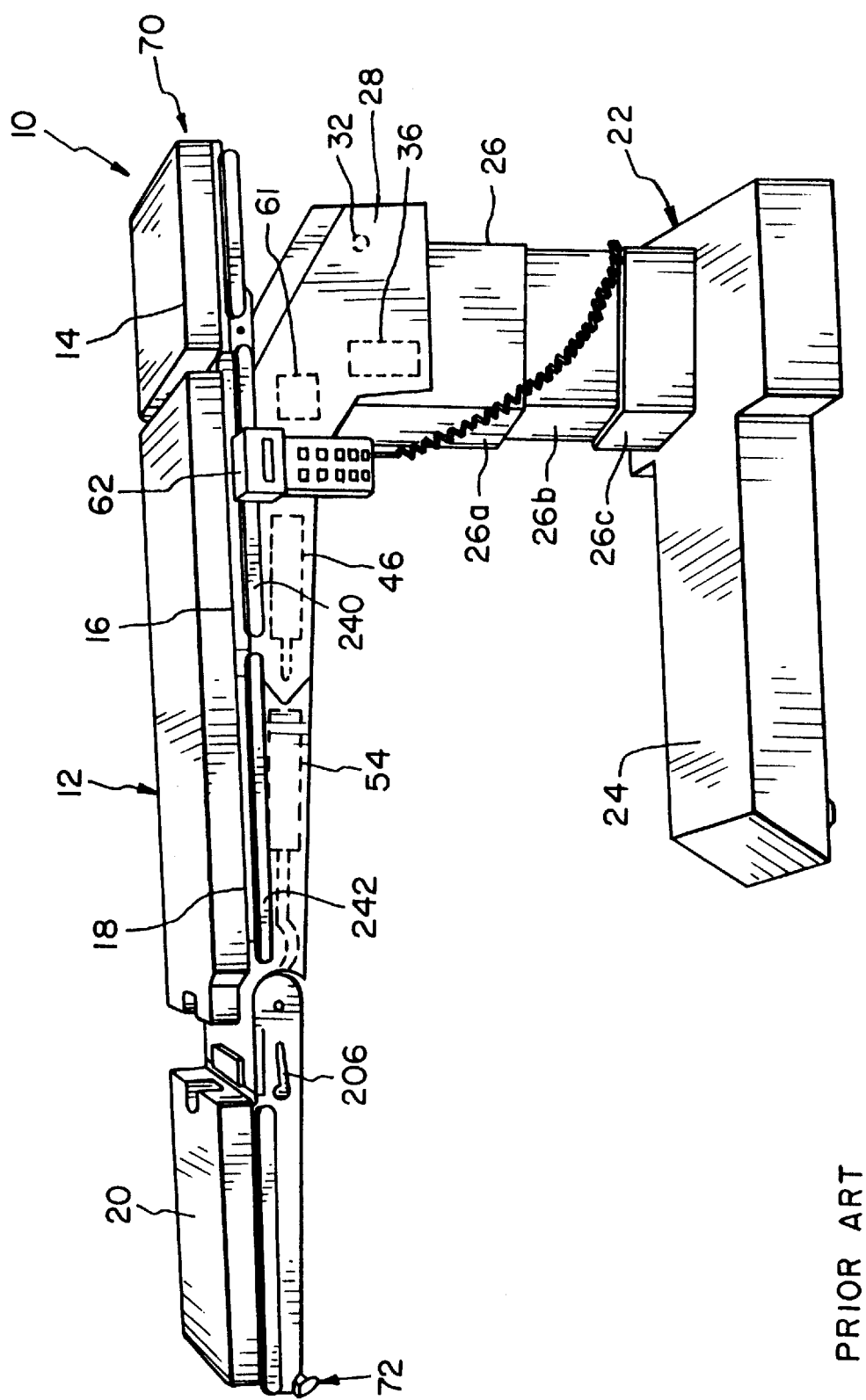
FIG. 1 is a perspective view of a surgical table in accordance with the prior art.
Figure 2:
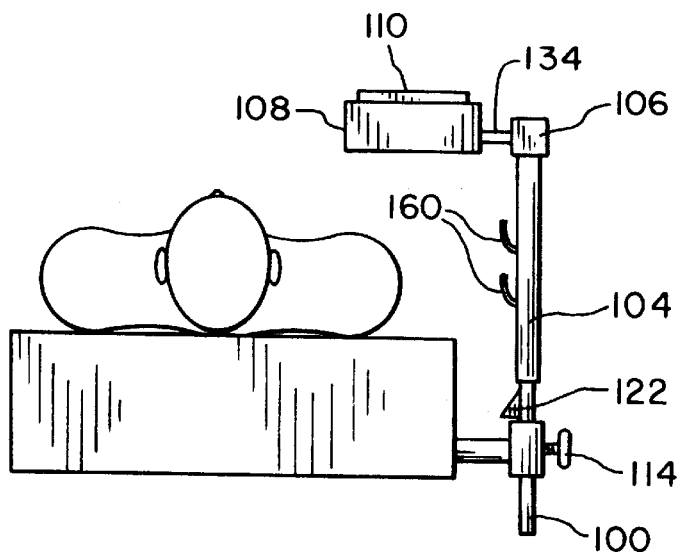
FIG. 2 is an end view of a surgical table and showing the surgical tray support system in accordance with the present invention.
Figure 3:
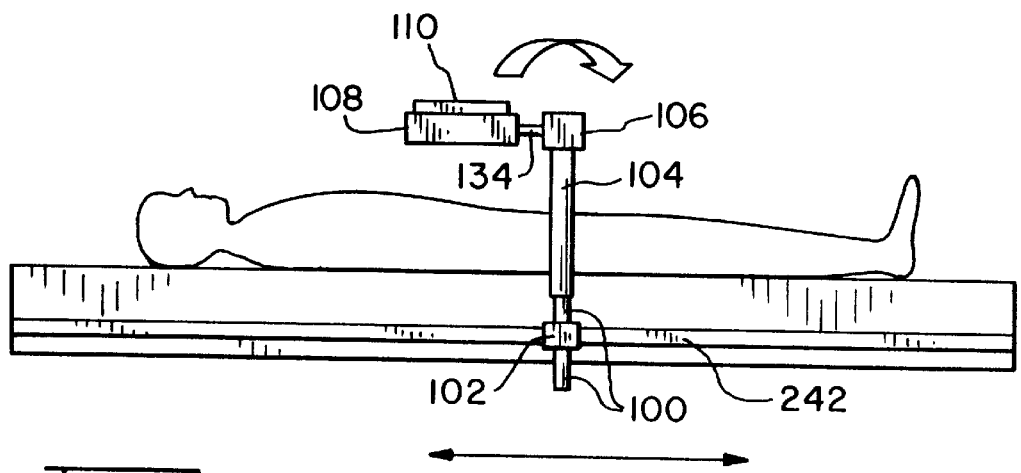
FIG. 3 is a side elevational view of a surgical tray support system in accordance with the present invention.

Referring to FIG. 1, which corresponds to FIG. 1 of U.S. Pat. No. 5,628,078, a typical surgical table 10 comprises a table top 12 formed of a plurality of interconnected articulated sections including a head section 14, a back section 16, a seat section 18 and a leg section 20. The table top 12 is supported on a support 22 including a base 24, a support column 26 extending upwardly from the base 24 and a support bridge 28 mounted to the top of the support column 26 and rigidly supporting the back section 16 of the table top 12.

The support column 26 is vertically extendable and includes telescoping sections 26a, 26b and 26c for providing upward and downward movement of the table top 12. The mechanism for providing the upward and downward movement of the support column 26 is conventional and known in the art.

The support bridge 28 is supported on the top of the column 26 for movement about a lateral tilt axis 30 and a longitudinal tilt axis (not shown). The bridge 28 is actuated for movement relative to the support column 26 by means of an actuator 34 causing the bridge and table top 12 to undergo lateral tilt movement about the axis 30, and an actuator 36 for causing the bridge 28 and table top 12 to undergo longitudinal tilt movement, such as for Trendelenburg positions, about the axis 32. The actuation mechanism for moving the bridge 28 relative to the column 26 is shown diagrammatically for illustrative purposes only and may comprise any known mechanism for tilting a surgical table about two axes.

The table top sections 14, 16, 18, 20 each include a frame supporting a support plate, and a cushion is attached to the upper surface of the support plate to provide a cushioned surface for a patient. Further, the table 10 is also designed as a cantilever structure with the back section 16, seat section 18 and leg section 20 extending in laterally spaced relation relative to the support column 26 to provide maximum clearance for performing x-ray procedures. Also, the section frame portions, including the back section engaging portions of the bridge 28, are located adjacent to the lateral edges of the table sections such that the central portions of the table sections are clear of obstruction, such as metal frame members, for facilitating performing radiographic procedures.

The table also includes one or more rail assemblies 240, 242 spaced from the sides of the table top. Rail assemblies 240, 242 typically are employed to support surgical accessories such as leg holders, arm supports, and the like. Such accessories commonly are supported on support rods which are in turn secured to the side rails. The support rods typically are clamped near one end of the side rails, and may include adjustable elbows defining portions which extend over the upper portions of the table to position the accessories. See, for example, U.S. Pat. No. 5,538,215.

In accordance with the present invention, there is provided a surgical tray support system for attachment to a surgical table support rail. Referring to FIGS. 2–5 and 7, a post 100 which may be round (FIG. 6A) or rectangular (FIG. 6B) in cross section is affixed by means of a bracket 102 to side rail 242. Bracket 102 may comprise a conventional rail clamp or the like which permits sliding adjustment along rail 242. A removable top tube 104 is slidably mounted over post 100. An elbow piece or block 106 is affixed to the top of tube 104. A frame 108 is in turn affixed to elbow 106 through a stub shaft 134. Elbow 106 includes a hole (shown in phantom at 130 in FIG. 5) for accommodating top tube 104, a hole 132 into which is rotatable mounted stub shaft 134, and one or more holes 136 for accommodating a locking pin 138 or the like slidably mounted on stub shaft 134, for permitting tilting adjusting of frame 108. Frame 108 is sized and shaped to accommodate a standard or custom surgical instrument tray 110 and to support the surgical tray by its side edges or rims. Alternatively, surgical tray 110 may be supported within frame 108 by means of bottom straps or rail members, or a perforated bottom bridging the frame walls.

Figure 8:
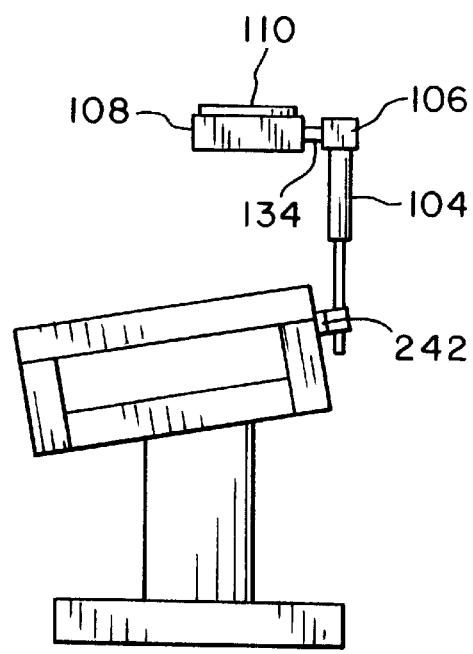
FIG. 8 is a view of an alternative support system in accordance with the present invention.
Figure 9:
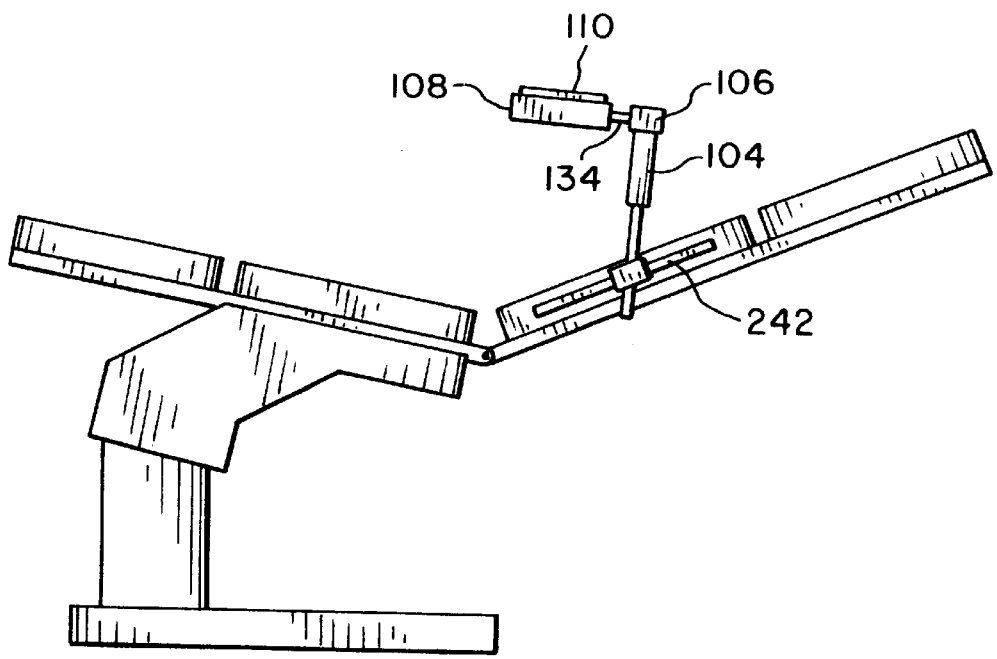
FIG. 9 is a side elevational view showing yet another embodiment of the present invention.

Preferably, bracket 102 includes a thumb screw 114 or the like to facilitate adjustment linearly along the side rails, and/or vertical adjustment of post 100. Also, if desired bracket 102 may comprise a rotatable joint having two, four or six degrees of adjustment freedom so that the support post 100 may be maintained in an essentially vertical orientation and adjusted up and down, and placement over to either side of the support post irrespective of the height and orientation of the operating table. This is illustrated, for example, in FIG. 8, where the surgical table is tilted to one side, or the table is articulated into an upward or downward position as shown in FIG. 9, to facilitate access to a patient and stability of the tray's contents.

A feature and advantage of the present invention is that it permits the surgical team to bring the surgical instruments closer to the patient, thus fostering efficiencies, and reducing possible accidental instrument drops. Yet, during a medical emergency, the trays readily may be swung out of the way or quickly or readily removed from the table altogether.

The top tube 104 and the tray frame 108 are made removable and preferably detachable from one another so that they may be sterilized in a conventional sterilizer, along with the loaded instrument trays, and delivered to the sterile field when the preperation is complete and the instruments are needed. Thus, sterility of the operating field is not compromised.

Figure 4:
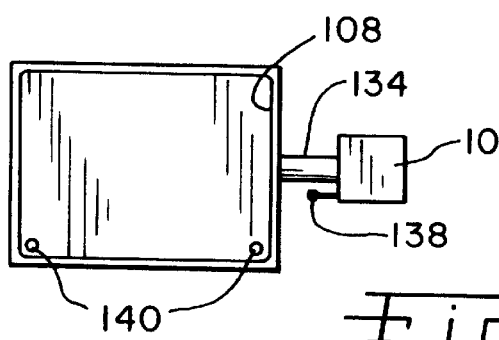
FIG. 4 is a top plan view of the frame and support elements of the surgical tray support assembly made in accordance with the present invention.
Figure 10:
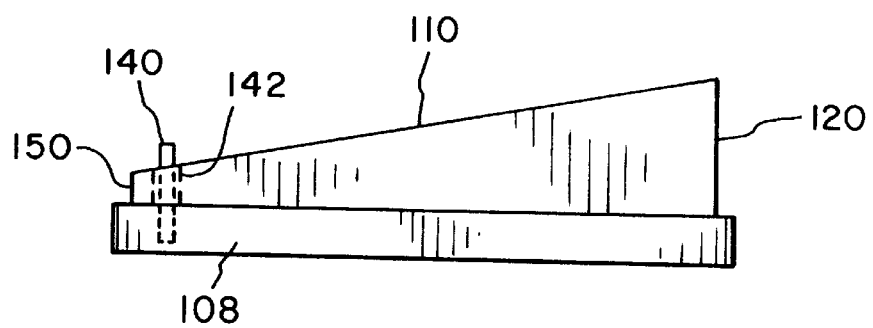
FIG. 10 is a view similar to FIG. 9, of still yet another embodiment of the present invention.

Various changes may be made in the foregoing invention without departing from the spirit and scope thereof. For example, referring to FIGS. 5 and 6, the posts may include one or more holes or stops 112, i.e. so that the tube and tray frame may be positively locked, e.g. by means of a removable pin or rod (122) at several fixed heights and/or selected swivel angles so as to accommodate surgical procedures, patient size, and surgeon/staff height. Also, if desired, cord or tubing management hooks 120 may be affixed to the tube top. In yet another embodiment of the invention, the surgical instrument tray support assembly of the present invention may be affixed to a Mayo stand or to a floor stand, whereby to present a greater number of appropriate instruments and supplies close to the operating field. Also, as shown in FIG. 10, the tray may be designed and manufactured to present at an angle by making the back wall thereof 120 higher than the front wall 122. And, as shown in FIGS. 4 and 10, one or more pins or keys 140 may be fixed in the frames 108 for cooperating with keyways or holes 142 formed through the trays for orienting and locking the trays in position in the frames.

There is thus provided a surgical instrument tray support assembly which brings the surgical instrument tray within easy reach and view of a surgical team without taking up valuable floor area around the operating table.

What is claimed is:

1. A surgical instrument tray support assembly for attachment to a base comprising:

a post;

a first bracket for attachment to a base for supporting said post in a generally upright position;

a top tube for slidably mounting over said post;

a frame for supporting a surgical tray;

a second bracket for attaching said frame to said top tube; and a lock for locking said surgical tray in said frame.

2. An assembly as claimed in claim 1 wherein said frame includes a pin for keying into a hole or keyway in said surgical tray carried in said frame.

3. A surgical instrument tray and support assembly for attachment to a base, comprising:

a post;

a surgical tray;

a first bracket for attachment to said base for supporting said post in a generally upright position;

a top tube for slidably mounting over said post;

a frame for supporting said surgical tray;

a second bracket for attaching said frame to said top tube; and a lock for locking said surgical tray in said frame.

4. A surgical instrument tray and support assembly for attachment to a base, comprising:

a post;

a surgical tray;

a first bracket for attachment to said base for supporting said post in a generally upright position;

a top tube for slidably mounting over said post;

a frame for supporting said surgical tray;

a second bracket for attaching said frame to said top tube; and a pin for keying into a hole or keyway in said surgical tray.

* * * * *

UNITED STATES PATENT AND TRADEMARK OFFICE
CERTIFICATE OF CORRECTION

PATENT NO. : 6,471,167 B1
DATED : October 29, 2002
INVENTOR(S) : Myers et al.

Page 1 of 1

It is certified that error appears in the above-identified patent and that said Letters Patent is hereby corrected as shown below:

Title page,
Item [56], References Cited, OTHER PUBLICATIONS, insert the following:
-- Midmark 7300 surgery table brochure, Midmark Corporation 1998 6 pgs
The Montreal Lateral Positioning Device, Midmark Corporation 1991 2 pgs --.

Column 1,
Line 26, insert the paragraphs beginning at column 2, Line 36 through Column 3, Line 19.

Column 2,
Line 56, delete "34"; and substitute therefore -- 61 --.

Column 3,
Line 64, delete "preparation"; and substitute therefore -- prep --.

Figure 5:
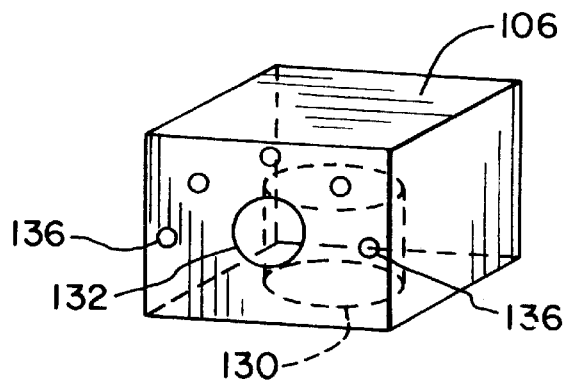
FIG. 5 is a perspective view showing details of the support post block element of the present invention.
Figure 6A:
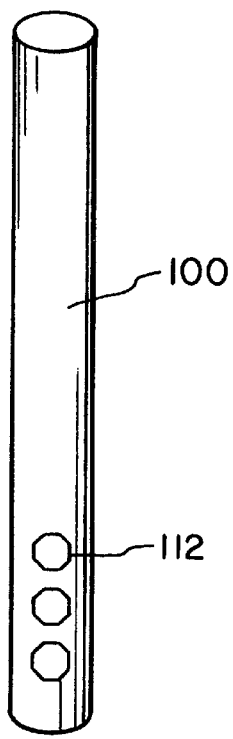
FIGS. 6A and B are side elevational views of support post portions of the present invention.
Figure 6B:
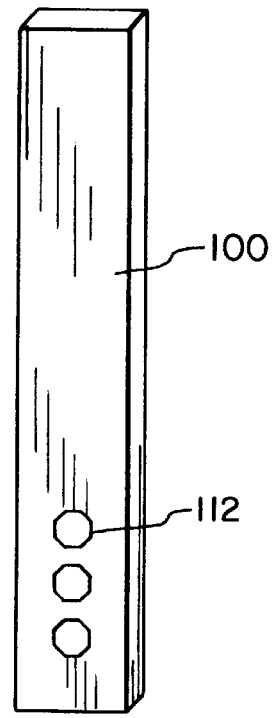
Figure 7:
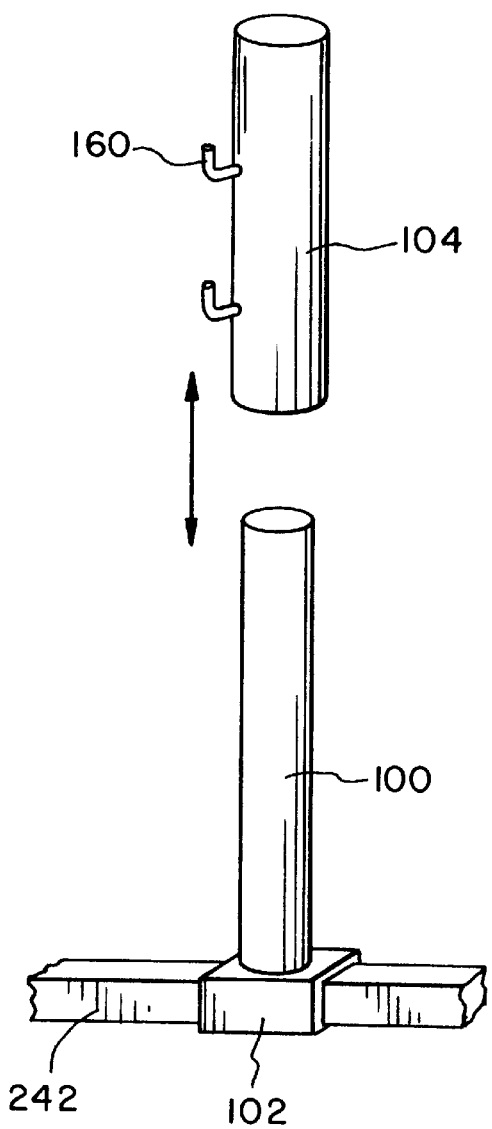
FIG. 7 is an exploded view of the support post and top tube portion of the support system in accordance with the present invention.

Column 4,
Line 3, delete "FIGS. 5 and 6,"; and substitute therefore -- FIGS. 6A and 6B, --;
Line 9, delete "120", and substitute therefore -- 160 --; and
Line 17, delete "122", and substitute therefore -- 150 --.

Signed and Sealed this

Sixth Day of July, 2004

JON W. DUDAS
*Acting Director of the United States Patent and Trademark Office*